United States Patent [19]
Winkelmann et al.

[11] B 3,992,397
[45] Nov. 16, 1976

[54] (1-ALKYL-5-NITRO-IMIDAZOLYL-2-ALKYL)-HETEROARYL COMPOUNDS AND PROCESS FOR THEIR MANUFACTURE

[75] Inventors: Erhardt Winkelmann, Kelkheim, Taunus; Wolfgang Raether, Dreieichenhain, both of Germany

[73] Assignee: Hoechst Aktiengesellschaft, Frankfurt am Main, Germany

[22] Filed: Dec. 12, 1974

[21] Appl. No.: 532,005

[44] Published under the second Trial Voluntary Protest Program on February 24, 1976 as document No. B 532,005.

[30] Foreign Application Priority Data
Dec. 14, 1973   Germany.............................. 2362171

[52] U.S. Cl. ........................... 260/308 D; 260/309; 260/310 R; 424/269; 424/273

[51] Int. Cl.² ....................................... C07D 257/04
[58] Field of Search ................................. 260/308 D

[56]          References Cited
          UNITED STATES PATENTS
3,574,195   4/1971   Hajeck ...................... 260/308 D X

*Primary Examiner*—Frederick E. Waddell
*Attorney, Agent, or Firm*—Curtis, Morris & Safford

[57]             ABSTRACT

New (1-alkyl-5-nitro-imidazolyl-2-alkyl)-heteroaryl compounds and process for their manufacture are described. The new compounds are well compatible and are effective against bacteria and protozoa as well as against fungi. They are especially active against trichomonads and amebae.

4 Claims, No Drawings

(1-ALKYL-5-NITRO-IMIDAZOLYL-2-ALKYL)-HETEROARYL COMPOUNDS AND PROCESS FOR THEIR MANUFACTURE

The present invention relates to (1-alkyl-5-nitro-imidazolyl-2-alkyl)-heteroaryl compounds and to a process for preparing them.

It is known to use 1-(2-hydroxyethyl)-2-methyl-5-nitroimidazole (Metronidazol) for the treatment of protozoal diseases, such as trichomoniasis and amebiasis.

Object of this invention are (1-alkyl-5-nitro-imidazolyl-2-alkyl)-heteroaryl sulfides, sulfoxides and sulfones of the formula I

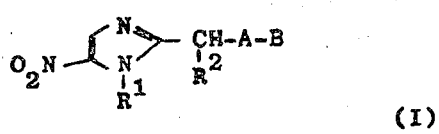

(I)

in which $R^1$ stands for a methyl or ethyl group, $R^2$ for a hydrogen atom or a methyl group, A for a sulfur bridge (—S—), a sulfoxide group (—SO—) or a sulfone group (—SO$_2$—) and B for a pyrazole ring

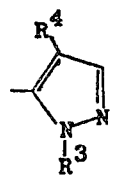

an imidazole ring

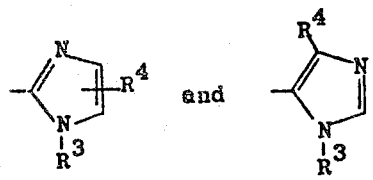

or a triazole ring

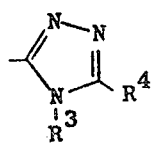

a tetrazole ring

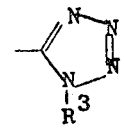

which can be linked in said manner to the sulfur bridge, sulfoxide group or sulfone group, and in which $R^3$ stands for a hydrogen atom, an alkyl group of 1 to 4 carbon atoms, preferably the methyl or ethyl group, or a phenyl group which may be substituted by a chlorine atom or a methyl group, and $R^4$ stands for a hydrogen atom, a methyl group, a cyano group, a nitro group or an amino group.

The new compounds are effective against various protozoa in particular against trichomonads and amebae, as well as against trypanosoma and bacteria.

Further object of this invention is a process for the manufacture of (1-alkyl-5-nitro-imidazolyl-2-alkyl)-heteroaryl sulfides, sulfoxides and sulfones of the above-said formula I, which comprises a. reacting a 1-alkyl-2-alkyl-5-nitro-imidazole of the formula II

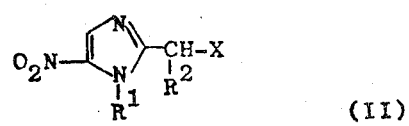

(II)

in which $R^1$ and $R^2$ are defined as above, and X stands for a halogen atom or an acyloxy group, preferably acetoxy, propoxy, butoxy, benzoyloxy, benzyloxy or tolyloxy, or an arylsulfonic acid ester group, preferably a benzene-sulfonic acid ester group, a toluenesulfonic acid ester group or a naphthalene-sulfonic acid ester group, with a heteroaryl mercaptane or the alkali metal or ammonium salt thereof corresponding to the formula III

Y - S - B (III)

in whch Y stands for hydrogen, an alkali metal, especially sodium or potassium, or ammonium and B is defined as above, or b. reacting a 1-alkyl-2-mercapto-alkyl-5-nitro-imidazole of the formula IV

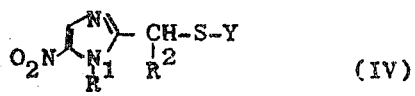

(IV)

in which $R^1$, $R^2$ and Y are defined as above, with a heteroaryl compound of the formula V

X - B (V)

in which X and B are defined as above, and where required oxidizing the sulfide compounds of formula I thus obtained to yield a sulfoxide or sulfone.

As starting substances of formula II, there are mentioned for example 1-methyl-, 1-ethyl-2-chloro-, -2-bromo-, -2-iodo-methyl- or 1-methyl-, 1-ethyl-2-chloro-, -2-bromo-, -2-iodo-(1-ethyl)-5-nitro-imidazole, 1-methyl- or 1-ethyl-2-acetoxy-5-nitroimidazole, or 1-methyl- or 1-ethyl-2-benzene- or -2-toluene-sulfonic acid ester.

As starting substances of formula III, there are mentioned, for example:

5-mercapto-pyrazole, 2-mercapto-imidazole, 4(5)-mercapto-imidazole, 2-mercapto-1,3,4-triazole, 2-mercapto-1,3,4,5-tetrazole, 1-methyl-or 1-phenyl-5-mercapto-pyrazole, -2-mercapto-imidazole, -4(5)-mercapto-imidazole, -2-mercapto-1,3,4-triazole, -2-mercapto-1,3,4,5-tetrazole.

4-cyano-, 4-nitro-5-mercapto-pyrazole, 4- or 5-nitro-2-mercapto-imidazole, 2-methyl-4(5)-mercapto-imidazole, 4- or 5-nitro-4(5)-mercapto-imidazole, 5-methyl-, 5-amino-2-mercapto-1,3,4-triazole, 1-methyl- or 1-phenyl-4-cyano-, -4-nitro-5-mercapto-pyrazole, 1-methyl- or 1-phenyl-4-nitro-2-mercapto-imidazole, 1-methyl- or 1-phenyl-5-nitro-2-mercapto-imidazole, 1-methyl- or 1-phenyl-2-methyl-4(5)-mercapto-imidazole, 1-methyl- or 1-phenyl-4-nitro-5-mercapto-imidazole, 1-methyl- or 1-phenyl-5-nitro-4-mercapto-imidazole, 1-methyl- or 1-phenyl-5-methyl-, -5-amino-2-mercapto-1,3,4-triazole.

Instead of the free mercapto compounds, the alkali metal or ammonium salts thereof, or mercaptane-yielding substances such as, for example, isothiouronium salt, may also be used.

As starting substances of formula IV, there are mentioned for example 1-methyl-, 1-ethyl-2-mercapto-methyl- or 1-methyl-, 1-ethyl-2-mercapto-(1-ethyl)-5-nitro-imidazoles or the alkali metal or ammonium salts thereof, or mercapto-yielding agents such as, for example, isothiouronium salts.

As starting compounds of formula V, there are mentioned for example all the compounds as mentioned for formula III, wherein, however, the mercapto group is replaced by a fluorine, chlorine, bromine or iodine atom, or an acetoxy-or benzene- or toluene-sulfonic acid ester grouping.

The 1-alkyl-2-chloroalkyl-nitro-imidazoles of formula II, used as starting compounds, are obtained by reacting 1-alkyl-2-hydroxy-alkyl-5-nitro-imidazoles with thionyl chloride and can be converted, where required, into fluorinated, brominated or iodinated compounds by a reaction with the corresponding metal halides.

The 1-alkyl-2-acyloxy-alkyl-5-nitro-imidazoles or 1-alkyl-2-(arylsulfonyloxy-alkyl)-5-nitro-imidazoles of formula II, also used as starting compounds, are obtained by reacting 1-alkyl-2-hydroxyalkyl-5-nitro-imidazoles with an acid anhydride or chloride, such as acetic anhydride or acetyl chloride, or with an arylsulfonic acid chloride, such as 4-toluene-sulfonic acid chloride.

The mercapto-heterocyclic compounds of formula III used as starting compounds are prepared by reacting corresponding halogeno-heterocyclic compounds with hydrogen sulfide.

The 1-alkyl-2-mercapto-alkyl-5-nitro-imidazoles of formula IV used as starting substances are obtained by reacting corresponding 1-alkyl-2-halogeno-alkyl-5-nitro-imidazoles with hydrogen sulfide.

The halogeno- or acyloxy-heterocyclic compounds of the formula V used as starting substances are prepared by reacting the corresponding hydroxy compounds with phosphorus halides or an acyl chloride.

The two variants (a) and (b) of the process of the invention are advantageously carried out using equimolar amounts of each starting substance, advantageously in a solvent or dispersing agent. When the free mercapto compounds of formula III or IV are used, the solvent used is preferably a polar one; when the salts thereof are used, the solvent chosen is preferably a non polar one.

As non polar solvents, there are mentioned, for example benzene, toluene, xylene or chlorobenzene. As polar solvents, there are mentioned, for example, alcohols, such as methanol, ethanol, propanol, butanol, methoxy-ethanol, or ketones, such as acetone, methylethyl-ketone, methylbutyl-ketone; further pyridine, picoline, quinoline, dimethylformamide, dimethyl-acetamide, N-methyl-pyrrolidone, tetramethyl-urea, hexamethyl-phosphoric acid triamide or dimethyl-sulfoxide.

The reaction temperatures may generally range from 0° to 150°C, preferably from 20° to 80°C. In this connection, the reactions using polar solvents may be carried out at lower temperatures, those using non-polar solvents suitably at elevated temperatures. Depending on the temperatures chosen, the reaction times range from a few minutes to several hours.

When the free mercapto compounds of formulae III and IV are used, it is advisable to use an acid-binding agent, such as as base, for example, triethylamine or pyridine, as well as alkali metal or alkaline earth metal carbonates and bicarbonates, hydroxides and alkoxides, for example the methoxides, ethoxides and butoxides.

The products of the invention are isolated according to the usual methods, for example by distilling off the solvents used or diluting the reaction solution with water. Where required, they may be purified by recrystallizing them from a mixture of appropriate solvents.

The sulfides of formula I (A = —S—), obtained according to one of the above-said process variants (a) or (b), may be converted by oxidation into the corresponding sulfoxides (A = —SO-) or sulfones (A = —SO$_2$—).

The oxidation reactions are advantageously carried out using simple or double molar amounts of an oxidizing agent. The treatment of the sulfides with one mol-equivalent of the oxidizing agent yields sulfoxides, with two mol-equivalents of oxidizing agent, it yields sulfones. As oxidizing agents, there may be used, for example hydrogen peroxide, or per-acids, such as peracetic acid, per-trifluoroacetic acid or metachloroperbenzoic acid, as well as nitric acid or chromic acid, or the salts thereof; moreover permanganates, hypochlorites, perchlorates, periodates and nitrogen oxides. The oxidation reactions are advantageously carried out in a solvent or dispersing agent.

For this purpose, these solvents are particularly useful which are not attacked by the oxidizing agent, for example acetic acid, or trifluoroacetic acid. When perbenzoic acid is used, methylene chloride or chloroform are also useful as solvents.

The oxidation reactions which are to yield sulfoxides are generally carried out at temperatures ranging from 10° to 30°C. The sulfones are generally obtained at oxidation temperatures of from 50° to 100°C. The sulfonyl compounds may be also prepared, where required by oxidation of the corresponding sulfonyl compounds by means of the specified oxidizing agents at elevated temperatures.

Depending on the temperature chosen and on the desired end product, the oxidation times range from a few minutes to some hours.

the products of the invention are isolated either by diluting the reaction solution with water and, at the same time, precipitating them or by evaporating the organic solvent in vacuo. They may also be purified, where required, by recrystallizing them from a suitable solvent or mixture of solvents.

The new compounds of formula I are well compatible and are effective against pathogens, such as bacteria and protozoa. They are especially active against trichomonads and amebae and are herein superior to the known Metronidazol.

The new compounds of formula I are therefore suitable for the treatment of protozoal diseases in mammals as caused, for example by infections with Trichomonas vaginalis and Entamoeba histolytica, as well as with trypanosoma cruci, trypanosoma bruoci and trypanosoma congolense, at a dosage of from 5 to 100 mg/kg of body weight.

The compounds of the invention can be administered orally or locally. The dosage unit forms for oral administration are usually tablets or capsules containing, per daily dosage unit, about 10 to 750 mg, preferably 150 to 500 mg, of the active ingredient, in admixture with a usual addition of diluents and/or extenders. For the local administration, jellies, powders, ointments of suppositories may be used.

EXAMPLES 1. 1-Methyl-2-(1-methyl-imidazolyl-2-thiomethyl)-5-nitro-imidazole 2.3 Grams (0.1 mol) of metallic sodium were dissolved in small portions in 50 ml of anhydrous methanol. Into this sodium methylate solution, 11.4 g (0.1 mol) of 1-methyl-2-mercapto-imidazole dissolved in 70 ml of anhydrous methanol were introduced, and the solution was concentrated by evaporation under reduced pressure. The residue was combined with a solution of 17.55 g (0.1 mol) of 1-methyl-2-chloromethyl-5-nitro-imidazole in 100 ml of dimethylacetamide, and the reaction mixture was heated to 40°C for one hour. After cooling, water was added to the solution until crystallization set in. The end product was suction-filtered and recrystallized from ethanol with an addition of charcoal.

In this manner, 20.0 g of 1-methyl-2-(1-methyl-imidazolyl-2-thiomethyl)-5-nitro-imidazole (corresponding to 79 % of the theoretical yield) were obtained in the form of yellowish crystals which melted at 155°C.

In an analogous manner, the following compounds were obtained with good yields:

2. 1-methyl-2-(1,3,4-triazolyl-2-thiomethyl)-5-nitro-imidazole, m.p. 170°C, from 1-methyl-2-chloromethyl-5-nitro-imidazole and 2-mercapto-1,3,4-triazole, 3. 1-methyl-2-(1-methyl-1,3,4,5-tetrazolyl-2-thiomethyl)-5-nitro-imidazole, m.p. 123°, from 1-methyl-2-chloro-methyl-5-nitro-imidazole and 1-methyl-2-mercapto-1,2,4,5-tetrazole, 4. 1-methyl-2-(1-phenyl-1,3,4,5-tetrazolyl-2-thiomethyl)-5-nitro-imidazole, m.p. 116°C, from 1-methyl-2-chloro-methyl-5-nitro-imidazole and 1-phenyl-2-mercapto-1,3,4,5-tetrazole, 5. 1-methyl-2-(5-methyl-1,3,4-triazolyl-2-thiomethyl)-5-nitro-imidazole, m.p. 168°C, from 1-methyl-2-chloro-methyl-5-nitro-imidazole and 5-methyl-2-mercapto-1,3,4-triazole, 6. 1-methyl-2-(5-amino-1,3,4-triazolyl-2-thiomethyl)-5-nitro-imidazole, m.p. 227°C, from 1-methyl-2-chloromethyl-5-nitro-imidazole and 5-amino-2-mercapto-1,3,4-triazole, 7. 1-methyl-2-(1-methyl-5-nitro-imidazolyl-2-thiomethyl)-5-nitro-imidazole, m.p. 263°C, from 1-methyl-2-chloro-methyl-5-nitro-imidazole and 1-methyl-5-nitro-2-mercapto-imidazole, 8. 1-ethyl-2-(1-methyl-imidazolyl-2-thiomethyl)-5-nitro-imidazole, m.p. 77°C, from 1-ethyl-2-chloromethyl-5-nitro-imidazole and 1-methyl-2-mercapto-imidazole, 9. 1-methyl-2-[1-methyl-imidazolyl-2-thio-(1-ethyl)]-5-nitro-imidazole, m.p. 73° – 75°C, from 1-methyl-2-chloro-(1-ethyl)-5-nitro-imidazole and 1-methyl-2-mercapto-imidazole.

10. 1-Methyl-2-(pyrazolyl-5-thiomethyl)-5-nitro-imidazole.

11. 1-Methyl-2-(imidazolyl-2-thiomethyl)-5-nitro-imidazole.

12. 1-Methyl-2-(imidazolyl-4(5)-thiomethyl)-5-nitro-imidazole.

13. 1-Methyl-2-(1,3,4,5-tetrazolyl-2-thiomethyl)-5-nitro-imidazole.

14. 1-Methyl-2-(1-methyl-pyrazolyl-5-thiomethyl)-5-nitro-imidazole.

15. 1-Methyl-2-(1-phenyl-pyrazolyl-5-thiomethyl)-5-nitro-imidazole.

16. 1-Methyl-2-(1-phenyl-imidazolyl-2-thiomethyl)-5-nitro-imidazole.

17. 1-Methyl-2-(1-methyl-imidazolyl-4(5)-thiomethyl)-5-nitro-imidazole.

18. 1-Methyl-2-(1-phenyl-imidazolyl-4(5)-thiomethyl)-5-nitro-imidazole.

19. 1-Methyl-2-(1-methyl-1,3,4-triazolyl-2-thiomethyl)-5-nitro-imidazole.

20. 1-Methyl-2-(1-phenyl-1,3,4-triazolyl-2-thiomethyl)-5-nitro-imidazole.

21. 1-Methyl-2-(4-cyano-pyrazolyl-5-thiomethyl)-5-nitro-imidazole.

22. 1-Methyl-2-(4-nitro-pyrazolyl-5-thiomethyl)-5-nitro-imidazole.

23. 1-Methyl-2-(4-nitro-imidazolyl-2-thiomethyl)-5-nitro-imidazole.

24. 1-Methyl-2-(5-nitro-imidazolyl-2-thiomethyl)-5-nitro-imidazole.

25. 1-Methyl-2-(2-methyl-imidazolyl-4(5)-thiomethyl)-5-nitro-imidazole.

26. 1-Methyl-2-(4-nitro-imidazolyl-5-thiomethyl)-5-nitro-imidazole.

27. 1-Methyl-2-(5-nitro-imidazolyl-4-thiomethyl)-5-nitro-imidazole.

28. 1-Methyl-2-(1-methyl-4-cyano-pyrazolyl-5-thiomethyl)-5-nitro-imidazole.

29. 1-Methyl-2-(1-phenyl-4-cyano-pyrazolyl-5-thiomethyl)-5-nitro-imidazole.

30. 1-Methyl-2-(1-methyl-4-nitro-pyrazolyl-5-thiomethyl)-5-nitro-imidazole.

31. 1-Methyl-2-(1-phenyl-4-nitro-pyrazolyl-5-thiomethyl)-5-nitro-imidazole.

32. 1-Methyl-2-(1-methyl-4-nitro-imidazolyl-2-thiomethyl)-5-nitro-imidazole.

33. 1-Methyl-2-(1-phenyl-4-nitro-imidazolyl-2-thiomethyl)-5-nitro-imidazole.

34. 1-Methyl-2-(1-phenyl-5-nitro-imidazolyl-2-thiomethyl)-5-nitro-imidazole.

35. 1-Methyl-2-(1-methyl-2-methyl-imidazolyl-4(5)-thiomethyl)-5-nitro-imidazole.

36. 1-Methyl-2-(1-phenyl-2-methyl-imidazolyl-4(5)-thiomethyl)-5-nitro-imidazole.
37. 1-Methyl-2-(1-methyl-4-nitro-imidazolyl-5-thiomethyl)-5-nitro-imidazole.
38. 1-Methyl-2-(1-phenyl-5-nitro-imidazolyl-4-thiomethyl)-5-nitro-imidazole.
39. 1-Methyl-2-(1-methyl-5-methyl-1,3,4-triazolyl-2-thiomethyl)-5-nitro-imidazole.
40. 1-Methyl-2-(1-phenyl-5-methyl-1,3,4-triazolyl-2-thiomethyl)-5-nitro-imidazole.
41. 1-Methyl-2-(1-methyl-5-amino-1,3,4-triazolyl-2-thiomethyl)-5-nitro-imidazole.
42. 1-Methyl-2-(1-phenyl-5-amino-1,3,4-triazolyl-2-thiomethyl)-5-nitro-imidazole.
43. 1-ethyl-2-(pyrazolyl-5-thiomethyl)-5-nitro-imidazole.
44. 1-ethyl-2-(imidazolyl-2-thiomethyl)-5-nitro-imidazole.
45. 1-ethyl-2-(imidazolyl-4(5)-thiomethyl)-5-nitro-imidazole.
46. 1-ethyl-2-(1,3,4-triazolyl-2-thiomethyl)-5-nitro-imidazole.
47. 1-ethyl-2-(1,3,4,5-tetrazolyl-2-thiomethyl)-5-nitro-imidazole.
48. 1-ethyl-2-(1-methyl-pyrazolyl-5-thiomethyl)-5-nitro-imidazole.
49. 1-ethyl-2-(1-phenyl-pyrazolyl-5-thiomethyl)-5-nitro-imidazole.
50. 1-ethyl-2-(1-phenyl-imidazolyl-2-thiomethyl)-5-nitro-imidazole.
51. 1-ethyl-2-(1-methyl-imidazolyl-4(5)-thiomethyl)-5-nitro-imidazole.
52. 1-ethyl-2-(1-phenyl-imidazolyl-4-(5)-thiomethyl)-5-nitro-imidazole.
53. 1-ethyl-2-(1-methyl-1,3,4-triazolyl-2-thiomethyl)-5-nitro-imidazole.
54. 1-ethyl-2-(1-phenyl-1,3,4-triazolyl-2-thiomethyl)-5-nitro-imidazole.
55. 1-ethyl-2-(1-methyl-1,3,4,5-tetrazolyl-2-thiomethyl)-5-nitro-imidazole.
56. 1-ethyl-2-(1-phenyl-1,3,4,5-tetrazolyl-2-thiomethyl)-5-nitro-imidazole.
57. 1-ethyl-2-(4-cyano-pyrazolyl-5-thiomethyl)-5-nitro-imidazole.
58. 1-ethyl-2-(4-nitro-pyrazolyl-5-thiomethyl)-5-nitro-imidazole.
59. 1-ethyl-2-(4-nitro-imidazolyl-2-thiomethyl)-5-nitro-imidazole.
60. 1-ethyl-2-(5-nitro-imidazolyl-2-thiomethyl)-5-nitro-imidazole.
61. 1-ethyl-2-(2-methyl-imidazolyl-4(5)-thiomethyl)-5-nitro-imidazole.
62. 1-ethyl-2-(4-nitro-imidazolyl-5-thiomethyl)-5-nitro-imidazole.
63. 1-ethyl-2-(5-nitro-imidazolyl-4-thiomethyl)-5-nitro-imidazole.
64. 1-ethyl-2-(5-methyl-1,3,4-triazolyl-2-thiomethyl)-5-nitro-imidazole.
65. 1-ethyl-2-(5-amino-1,3,4-triazolyl-2-thiomethyl)-5-nitro-imidazole.
66. 1-ethyl-2-(1-methyl-4-cyano-pyrazolyl-5-thiomethyl)-5-nitro-imidazole.
67. 1-ethyl-2-(1-phenyl-4-cyano-pyrazolyl-5-thiomethyl)-5-nitro-imidazole.
68. 1-ethyl-2-(1-methyl-4-nitro-pyrazolyl-5-thiomethyl)-5-nitro-imidazole.
69. 1-ethyl-2-(1-phenyl-4-nitro-pyrazolyl-5-thiomethyl)-5-nitro-imidazole.
70. 1-ethyl-2-(1-methyl-4-nitro-imidazolyl-2-thiomethyl)-5-nitro-imidazole.
71. 1-ethyl-2-(1-phenyl-4-nitro-imidazolyl-2-thiomethyl)-5-nitro-imidazole.
72. 1-ethyl-2-(1-methyl-5-nitro-imidazolyl-2-thiomethyl)-5-nitro-imidazole.
73. 1-ethyl-2-(1-phenyl-5-nitro-imidazolyl-2-thiomethyl)-5-nitro-imidazole.
74. 1-ethyl-2-(1-methyl-2-methyl-imidazolyl-4(5)-thiomethyl)-5-nitro-imidazole.
75. 1-ethyl-2-(1-phenyl-2-methyl-imidazolyl-4(5)-thiomethyl)-5-nitro-imidazole.
76. 1-ethyl-2-(1-methyl-4-nitro-imidazolyl-5-thiomethyl)-5-nitro-imidazole.
77. 1-ethyl-2-(1-phenyl-5-nitro-imidazolyl-4-thiomethyl)-5-nitro-imidazole.
78. 1-ethyl-2-(1-methyl-5-methyl-1,3,4-triazolyl-2-thiomethyl)-5-nitro-imidazole.
79. 1-ethyl-2-(1-phenyl-5-methyl-1,3,4-triazolyl-2-thiomethyl)-5-nitro-imidazole.
80. 1-ethyl-2-(1-methyl-5-amino-1,3,4-triazolyl-2-thiomethyl)-5-nitro-imidazole.
81. 1-ethyl-2-(1-phenyl-5-amino-1,3,4-triazolyl-2-thiomethyl)-5-nitro-imidazole.
82. 1-Methyl-2-[pyrazolyl-5-thio-(1-ethyl)]-5-nitro-imidazole.
83. 1-Methyl-2-[imidazolyl-2-thio-(1-ethyl)]-5-nitro-imidazole.
84. 1-Methyl-2-[imidazolyl-4(5)-thio-(1-ethyl)]-5-nitro-imidazole.
85. 1-Methyl-2-[1,3,4-triazolyl-2-thio-(1-ethyl)]-5-nitro-imidazole.
86. 1-Methyl-2-[1,3,4,5-tetrazolyl-2-thio-(1-ethyl)]-5-nitro-imidazole.
87. 1-Methyl-2-[1-methyl-pyrazolyl-5-thio-(1-ethyl)]-5-nitro-imidazole.
88. 1-Methyl-2-[1-phenyl-pyrazolyl-5-thio-(1-ethyl)]-5-nitro-imidazole.
89. 1-Methyl-2-[1-phenyl-imidazolyl-2-thio-(1-ethyl)]-5-nitro-imidazole.
90. 1-Methyl-2-[1-methyl-imidazolyl-4(5)-thio-(1-ethyl)]-5-nitro-imidazole.
91. 1-Methyl-2-[1-phenyl-imidazolyl-4(5)-thio-(1-ethyl)]-5-nitro-imidazole.
92. 1-Methyl-2-[1-methyl-1,3,4-triazolyl-2-thio-(1-ethyl)]-5-nitro-imidazole.
93. 1-Methyl-2-[1-phenyl-1,3,4-triazolyl-2-thio-(1-ethyl)]-5-nitro-imidazole.
94. 1-Methyl-2-[1-methyl-1,3,4,5-tetrazolyl-2-thio-(1-ethyl)]-5-nitro-imidazole.
95. 1-Methyl-2-[1-phenyl-1,3,4,5-tetrazolyl-2-thio-(1-ethyl)]-5-nitro-imidazole.
96. 1-Methyl-2-[4-cyano-pyrazolyl-5-thio-(1-ethyl)]-5-nitro-imidazole.
97. 1-Methyl-2-[4-nitro-pyrazolyl-5-thio-(1-ethyl)]-5-nitro-imidazole.
98. 1-Methyl-2-[4-nitro-imidazolyl-2-thio-(1-ethyl)]-5-nitro-imidazole.
99. 1-Methyl-2-[5-nitro-imidazolyl-2-thio-(1-ethyl)]-5-nitro-imidazole.
100. 1-Methyl-2-[2-methyl-imidazolyl-4(5)-thio-(1-ethyl)]-5-nitro-imidazole.
101. 1-Methyl-2-[4-nitro-imidazolyl-5-thio-(1-ethyl)]-5-nitro-imidazole.
102. 1-Methyl-2-[5-nitro-imidazolyl-4-thio-(1-ethyl)]-5-nitro-imidazole.
103. 1-Methyl-2-[5-methyl-1,3,4-triazolyl-2-thio-(1-ethyl)]-5-nitro-imidazole.

104. 1-Methyl-2-[5-amino-1,3,4-triazolyl-2-thio-(1-ethyl)]-5-nitro-imidazole.

105. 1-Methyl-2-[1-methyl-4-cyano-pyrazolyl-5-thio-(1-ethyl)]-5-nitro-imidazole.

106. 1-Methyl-2-[1-phenyl-4-cyano-pyrazolyl-5-thio-(1-ethyl)]-5-nitro-imidazole.

107. 1-Methyl-2-[1-methyl-4-nitro-pyrazolyl-5-thio-(1-ethyl)]-5-nitro-imidazole.

108. 1-Methyl-2-[1-phenyl-4-nitro-pyrazolyl-5-thio-(1-ethyl)]-5-nitro-imidazole.

109. 1-Methyl-2-[1-methyl-4-nitro-imidazolyl-2-thio-(1-ethyl)]-5-nitro-imidazole.

110. 1-Methyl-2-[1-phenyl-4-nitro-imidazolyl-2-thio-(1-ethyl)]-5-nitro-imidazole.

111. 1-Methyl-2-[1-methyl-5-nitro-imidazolyl-2-thio-(1-ethyl)]-5-nitro-imidazole.

112. 1-Methyl-2-[1-phenyl-5-nitro-imidazolyl-2-thio-(1-ethyl)]-5-nitro-imidazole.

113. 1-Methyl-2-[1-methyl-2-methyl-imidazolyl-4(5)-thio-(1-ethyl)]-5-nitro-imidazole.

114. 1-Methyl-2-[1-phenyl-2-methyl-imidazolyl-4(5)-thio-(1-ethyl)]-5-nitro-imidazole.

115. 1-Methyl-2-[1-methyl-4-nitro-imidazolyl-5-thio-(1-ethyl)]-5-nitro-imidazole.

116. 1-Methyl-2-[1-phenyl-5-nitro-imidazolyl-4-thio-(1-ethyl)]-5-nitro-imidazole.

117. 1-Methyl-2-[1-methyl-5-methyl-1,3,4-triazolyl-2-thio-(1-ethyl)]-5-nitro-imidazole.

118. 1-Methyl-2-[1-phenyl-5-methyl-1,3,4-triazolyl-2-thio-(1-ethyl)]-5-nitro-imidazole.

119. 1-Methyl-2-[1-methyl-5-amino-1,3,4-triazolyl-2-thio-(1-ethyl)]-5-nitro-imidazole.

120. 1-Methyl-2-[1-phenyl-5-amino-1,3,4-triazolyl-2-thio-(1-ethyl)]-5-nitro-imidazole.

121.
1-Methyl-2-(1-methyl-imidazolyl-2-sulfinylmethyl)-5-nitro-imidazole 25.3 Grams (0.1 mol) of 1-methyl-2-(1-methyl-imidazolyl-2-thiomethyl)-5-nitro-imidazole were dissolved in 200 ml of chloroform, and a solution of 17.25 g (0.1 mol) of m-chloro-perbenzoic acid in 50 ml of chloroform was added dropwise while stirring at room temperature. The reaction solution was then stirred for another hour at room temperature, shaken with dilute sodium carbonate solution, the chloroform phase was separated, the solution was dried over sodium sulfate and evaporated. The residue was recrystallized from an alcohol.

Thus, 17.8 g of 1-methyl-2-(1-methyl-imidazolyl-2-sulfinylmethyl)-5-nitro-imidazole (corresponding to 66 % of the theoretical yield) were obtained in the form of yellowish crystals which melted at 170°C.

In an analogous manner, the following compounds were obtained in good yield from the corresponding thio compounds:

122. 1-Methyl-2-(pyrazolyl-5-sulfinylmethyl)-5-nitro-imidazole.

123. 1-Methyl-2-(imidazolyl-2-sulfinylmethyl)-5-nitro-imidazole.

124. 1-Methyl-2-(imidazolyl-4(5)-sulfinylmethyl)-5-nitro-imidazole.

125. 1-Methyl-2-(1,3,4-triazolyl-2-sulfinylmethyl)-5-nitro-imidazole.

126. 1-Methyl-2-(1,3,4,5-tetrazolyl-2-sulfinylmethyl)-5-nitro-imidazole.

127. 1-Methyl-2-(1-methyl-pyrazolyl-5-sulfinylmethyl)-5-nitro-imidazole.

128. 1-Methyl-2-(1-phenyl-pyrazolyl-5-sulfinylmethyl)-5-nitro-imidazole.

129. 1-Methyl-2-(1-phenyl-imidazolyl-2-sulfinylmethyl)-5-nitro-imidazole.

130. 1-Methyl-2-(1-methyl-imidazolyl-4(5)-sulfinylmethyl)-5-nitro-imidazole.

131. 1-Methyl-2-(1-phenyl-imidazolyl-4(5)-sulfinylmethyl)-5-nitro-imidazole.

132. 1-Methyl-2-(1-methyl-1,3,4-triazolyl-2-sulfinylmethyl)-5-nitro-imidazole.

133. 1-Methyl-2-(1-phenyl-1,3,4-triazolyl-2-sulfinylmethyl)-5-nitro-imidazole.

134. 1-Methyl-2-(1-methyl-1,3,4,5-tetrazolyl-2-sulfinylmethyl)-5-nitro-imidazole.

135. 1-Methyl-2-(1-phenyl-1,3,4,5-tetrazolyl-2-sulfinylmethyl)-5-nitro-imidazole.

136. 1-Methyl-2-(2-methyl-imidazolyl-4(5)-sulfinylmethyl)-5-nitro-imidazole.

137. 1-Methyl-2-(5-methyl-1,3,4-triazolyl-2-sulfinylmethyl)-5-nitro-imidazole.

138. 1-Methyl-2-(1-methyl-2-methyl-imidazolyl-4(5)-sulfinylmethyl)-5-nitro-imidazole.

139. 1-Methyl-2-(1-phenyl-2-methyl-imidazolyl-4(5)-sulfinylmethyl)-5-nitro-imidazole.

140. 1-Methyl-2-(1-methyl-5-methyl-1,3,4-triazolyl-2-sulfinylmethyl)-5-nitro-imidazole.

141. 1-Methyl-2-(1-phenyl-5-methyl-1,3,4-triazolyl-2-sulfinylmethyl)-5-nitro-imidazole.

142. 1-ethyl-2-(pyrazolyl-5-sulfinylmethyl)-5-nitro-imidazole.

143. 1-ethyl-2-(imidazolyl-2-sulfinylmethyl)-5-nitro-imidazole.

144. 1-ethyl-2-(imidazolyl-4(5)-sulfinylmethyl)-5-nitro-imidazole.

145. 1-ethyl-2-(1,3,4-triazolyl-2-sulfinylmethyl)-5-nitro-imidazole.

146. 1-ethyl-2-(1,3,4,5-tetrazolyl-2-sulfinylmethyl)-5-nitro-imidazole.

147. 1-ethyl-2-(1-methyl-pyrazolyl-5-sulfinylmethyl)-5-nitro-imidazole.

148. 1-ethyl-2-(1-phenyl-pyrazolyl-5-sulfinylmethyl)-5-nitro-imidazole.

149. 1-ethyl-2-(1-methyl-imidazolyl-2-sulfinylmethyl)-5-nitro-imidazole.

150. 1-ethyl-2-(1-phenyl-imidazolyl-2-sulfinylmethyl)-5-nitro-imidazole.

151. 1-ethyl-2-(1-methyl-imidazolyl-4(5)-sulfinylmethyl)-5-nitro-imidazole.

152. 1-ethyl-2-(1-phenyl-imidazolyl-4(5)-sulfinylmethyl)-5-nitro-imidazole.

153. 1-ethyl-2-(1-methyl-1,3,4-triazolyl-2-sulfinylmethyl)-5-nitro-imidazole.

154. 1-ethyl-2-(1-phenyl-1,3,4-triazolyl-2-sulfinylmethyl)-5-nitro-imidazole.

155. 1-ethyl-2-(1-methyl-1,3,4,5-tetrazolyl-2-sulfinylmethyl)-5-nitro-imidazole.

156. 1-ethyl-2-(1-phenyl-1,3,4,5-tetrazolyl-2-sulfinylmethyl)-5-nitro-imidazole.

157. 1-Methyl-2-[pyrazolyl-5-sulfinyl-(1-ethyl)]-5-nitro-imidazole.

158. 1-Methyl-2-[imidazolyl-2-sulfinyl-(1-ethyl)]-5-nitro-imidazole.

159. 1-Methyl-2-[imidazolyl-4(5)-sulfinyl-(1-ethyl)]-5-nitro-imidazole.

160. 1-Methyl-2-[1,3,4-triazolyl-2-sulfinyl-(1-ethyl)]-5-nitro-imidazole.

161. 1-Methyl-2-[1,3,4,5-tetrazolyl-2-sulfinyl-(1-ethyl)]-5-nitro-imidazole.

162. 1-Methyl-2-[1-methyl-pyrazolyl-5-sulfinyl-(1-ethyl)]-5-nitro-imidazole.
163. 1-Methyl-2-[1-phenyl-pyrazolyl-5-sulfinyl-(1-ethyl)]-5-nitro-imidazole.
164. 1-Methyl-2-[1-methyl-imidazolyl-2-sulfinyl-(1-ethyl)]-5-nitro-imidazole.
165. 1-Methyl-2-[1-phenyl-imidazolyl-2-sulfinyl-(1-ethyl)]-5-nitro-imidazole.
166. 1-Methyl-2-[1-methyl-imidazolyl-4(5)-sulfinyl-(1-ethyl)]-5-nitro-imidazole.
167. 1-Methyl-2-[1-phenyl-imidazolyl-4(5)-sulfinyl-(1-ethyl)]-5-nitro-imidazole.
168. 1-Methyl-2-[1-methyl-1,3,4-triazolyl-2-sulfinyl-(1-ethyl)]-5-nitro-imidazole.
169. 1-Methyl-2-[1-phenyl-1,3,4-triazolyl-2-sulfinyl-(1-ethyl)]-5-nitro-imidazole.
170. 1-Methyl-2-[1-methyl-1,3,4,5-tetrazolyl-2-sulfinyl-(1-ethyl)]-5-nitro-imidazole.
171. 1-Methyl-2-[1-phenyl-1,3,4,5-tetrazolyl-2-sulfinyl-(1-ethyl)]-5-nitro-imidazole.

172.
1-Methyl-2-(1-methyl-imidazolyl-2-sulfonylmethyl)-5-nitro-imidazole 25.3 Grams (0.1 mol) of 1-methyl-2-(1-methyl-imidazolyl-2-thio-methyl)-5-nitro-imidazole were dissolved in 400 ml of glacial acetic acid, and 20.0 ml (0.2 mol) of 35 % hydrogen peroxide were added dropwise while stirring at room temperature. The reaction was not exothermic. Stirring was then continued for 2 hours while heating on a steam bath. The reaction solution was concentrated by evaporation under reduced pressure, and the residue was recrystallized from water/alcohol. In this manner, 22.2 g of 1-methyl-2-(1-methyl-imidazolyl-2-sulfonylmethyl)-5-nitro-imidazole (corresponding to 78 % of the theoretical yield) were obtained in the form of yellowish crystals which melted at 193°C.

In an analogous manner, the following compounds were obtained in good yields from the corresponding thio compounds:
173. 1-Methyl-2-(pyrazolyl-5-sulfonylmethyl)-5-nitro-imidazole.
174. 1-Methyl-2-(imidazolyl-2-sulfonylmethyl)-5-nitro-imidazole.
175. 1-Methyl-2-(imidazolyl-4(5)-sulfonylmethyl)-5-nitro-imidazole.
176. 1-Methyl-2-(1,3,4-triazolyl-2-sulfonylmethyl)-5-nitro-imidazole.
177. 1-Methyl-2-(1,3,4,5-tetrazolyl-2-sulfonylmethyl)-5-nitro-imidazole.
178. 1-Methyl-2-(1-methyl-pyrazolyl-5-sulfonylmethyl)-5-nitro-imidazole.
179. 1-Methyl-2-(1-phenyl-pyrazolyl-5-sulfonylmethyl)-5-nitro-imidazole.
180. 1-Methyl-2-(1-phenyl-imidazolyl-2-sulfonylmethyl)-5-nitro-imidazole.
181. 1-Methyl-2-(1-methyl-imidazolyl-4(5)-sulfonylmethyl)-5-nitro-imidazole.
182. 1-Methyl-2-(1-phenyl-imidazolyl-4(5)-sulfonylmethyl)-5-nitro-imidazole.
183. 1-Methyl-2-(1-methyl-1,3,4-triazolyl-2-sulfonylmethyl)-5-nitro-imidazole.
184. 1-Methyl-2-(1-phenyl-1,3,4-triazolyl-2-sulfonylmethyl)-5-nitro-imidazole.
185. 1-Methyl-2-(1-methyl-1,3,4,5-tetrazolyl-2-sulfonylmethyl)-5-nitro-imidazole.
186. 1-Methyl-2-(1-phenyl-1,3,4,5-tetrazolyl-2-sulfonylmethyl)-5-nitro-imidazole.
187. 1-Methyl-2-(2-methyl-imidazolyl-4(5)-sulfonylmethyl)-5-nitro-imidazole.
188. 1-Methyl-2-(5-methyl-1,3,4-triazolyl-2-sulfonylmethyl)-5-nitro-imidazole.
189. 1-Methyl-2-(1-methyl-2-methyl-imidazolyl-4(5)-sulfonylmethyl)-5-nitro-imidazole.
190. 1-Methyl-2-(1-phenyl-2-methyl-imidazolyl-4(5)-sulfonylmethyl)-5-nitro-imidazole.
191. 1-Methyl-2-(1-methyl-5-methyl-1,3,4-triazolyl-2-sulfonylmethyl)-5-nitro-imidazole.
192. 1-Methyl-2-(1-phenyl-5-methyl-1,3,4-triazolyl-2-sulfonyl-methyl)-5-nitro-imidazole.
193. 1-ethyl-2-(pyrazolyl-5-sulfonylmethyl)-5-nitro-imidazole.
194. 1-ethyl-2-(imidazolyl-2-sulfonylmethyl)-5-nitro-imidazole.
195. 1-ethyl-2-(imidazolyl-4(5)-sulfonylmethyl)-5-nitro-imidazole.
196. 1-ethyl-2-(1,3,4-triazolyl-2-sulfonylmethyl)-5-nitro-imidazole.
197. 1-ethyl-2-(1,3,4,5-tetrazolyl-2-sulfonylmethyl)-5-nitro-imidazole.
198. 1-ethyl-2-(1-methyl-pyrazolyl-5-sulfonylmethyl)-5-nitro-imidazole.
199. 1-ethyl-2-(1-phenyl-pyryzolyl-5-sulfonylmethyl)-5-nitro-imidazole.
200. 1-ethyl-2-(1-methyl-imidazolyl-2-sulfonylmethyl)-5-nitro-imidazole.
201. 1-ethyl-2-(1-phenyl-imidazolyl-2-sulfonylmethyl)-5-nitro-imidazole.
202. 1-ethyl-2-(1-methyl-imidazolyl-4(5)-sulfonylmethyl)-5-nitro-imidazole.
203. 1-ethyl-2-(1-phenyl-imidazolyl-4(5)-sulfonylmethyl)-5-nitro-imidazole.
204. 1-ethyl-2-(1-methyl-1,3,4-triazolyl-2-sulfonylmethyl)-5-nitro-imidazole.
205. 1-ethyl-2-(1-phenyl-1,3,4-trizolyl-2-sulfonylmethyl)-5-nitro-imidazole.
206. 1-ethyl-2-(1-methyl-1,3,4,5-tetrazolyl-2-sulfonylmethyl)-5-nitro-imidazole.
207. 1-ethyl-2-(1-phenyl-1,3,4,5-tetrazolyl-2-sulfonylmethyl)-5-nitro-imidazole.
208. 1-Methyl-2-[pyrazolyl-5-sulfinyl-(1-ethyl)]-5-nitro-imidazol.
209. 1-Methyl-2-[imidazolyl-2-sulfinyl-(1-ethyl)]-5-nitro-imidazole.
210. 1-Methyl-2-[imidazolyl-4(5)-sulfinyl-(1-ethyl)]-5-nitro-imidazole.
211. 1-Methyl-2-[1,3,4-triazolyl-2-sulfinyl-(1-ethyl)]-5-nitro-imidazole.
212. 1-Methyl-2-[1,3,4,5-tetrazolyl-2-sulfinyl-(1-ethyl)]-5-nitro-imidazole.
213. 1-Methyl-2-[1-methyl-pyrazolyl-5-sulfinyl-(1-ethyl)]-5-nitro-imidazole.
214. 1-Methyl-2-[1-phenyl-pyryzolyl-5-sulfinyl-(1-ethyl)]-5-nitro-imidazole.
215. 1-Methyl-2-[1-methyl-imidazolyl-2-sulfinyl-(1-ethyl)]-5-nitro-imidazole.
216. 1-Methyl-2-[1-phenyl-imidazolyl-2-sulfinyl-(1-ethyl)]-5-nitro-imidazole.
217. 1-Methyl-2-[1-methyl-imidazolyl-4(5)-sulfinyl-(1-ethyl)]-5-nitro-imidazole.
218. 1-Methyl-2-[1-phenyl-imidazolyl-4(5)-sulfinyl-(1-ethyl)]-5-nitro-imidazole.
219. 1-Methyl-2-[1-methyl-1,3,4-triazolyl-2-sulfinyl-(1-ethyl)]-5-nitro-imidazole.

220. 1-Methyl-2-[1-phenyl-1,3,4-triazolyl-2-sulfinyl-(1-ethyl)]-5-nitro-imidazole.

221. 1-Methyl-2-[1-methyl-1,3,4,5-tetrazolyl-2-sulfinyl-(1-ethyl)]-5-nitro-imidazole.

222. 1-Methyl-2-[1-phenyl-1,3,4,5-tetrazolyl-2-sulfinyl-(1-ethyl)]-5-nitro-imidazole.

223. (Alternative method b)

1-methyl-2-(1-methyl-imidazolyl-2-thiomethyl)-5-nitro-imidazole

Equimolar amounts (0.1 mol) of 1-methyl-2-(S-isothio-uronium-methyl)-5-nitro-imidazole hydrochloride and 2-chloro-1-methyl-imidazole or 2-bromo-1-methyl-imidazole were heated in dimethyl-formamide to 35° – 45°C for 1 hour in the presence of 2 mol-equivalents of sodium methylate. After cooling and addition of about the same amount of water, 1-methyl-2-(1-methyl-imidazolyl-2-thiomethyl)-5-nitro-imidazole was obtained, melting point: 155°C. The 1-methyl-2-(S-isothiouronium-methyl)-5-nitro-imidazole hydrochloride used as starting product is known from German Offenlegungsschrift No. 2,124,103 and was prepared by reacting 1-methyl-2-chloromethyl-5-nitro-imidazole with thio-urea. In an analogous manner, the compounds mentioned in the above Examples 2 to 222 were obtained.

The 1-alkyl-2-chloroalkyl-5-nitro-imidazoles used as starting compounds were prepared according to known methods by reacting 1-alkyl-2-hydroxyalkyl-5-nitro-imidazoles with thionyl chloride.

The 1-alkyl-2-acetoxyalkyl-5-nitro-imidazoles or 1-alkyl-2-(4-toluylsulfonyloxy-alkyl)-5-nitro-imidazoles used as starting compounds were prepared according to known methods by reactin 1-alkyl-2-hydroxyalkyl-5-nitro-imidazoles with acetic acid anhydride or acetyl chloride or with 4-toluene-sulfonic acid chloride.

The mercapto-heterocyclic compounds used as starting compounds are either known in the art or can be prepared according to known methods from the corresponding halogeno-heretocyclic compounds.

We claim:

1. A (1-alkyl-5-nitro-imidazolyl-2-alkyl)-heteroaryl sulfide, sulfoxide or sulfone of the formula

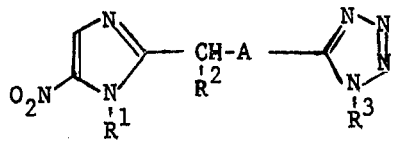

in which $R^1$ stands for methyl or ethyl, $R^2$ stands for hydrogen or methyl, $R^3$ stands for hydrogen, alkyl of 1 to 4 carbon atoms, phenyl, tolyl or chlorophenyl, and A stands for sulfur (—S—), sulfoxide (—SO—) or sulfone (—SO$_2$—).

2. A compound as defined in claim 1 in which $R^3$ is methyl or ethyl.

3. A compound as claimed in claim 1, which is 1-methyl-2-(1-methyl-1,3,4,5-tetrazolyl-2-thiomethyl)-5-nitro-imidazole.

4. A compound as claimed in claim 1, which is 1-methyl-2-(1-phenyl-1,3,4,5-tetrazolyl-2-thiomethyl)-5-nitro-imidazole.

* * * * *